(12) United States Patent
Kwon et al.

(10) Patent No.: US 12,427,510 B2
(45) Date of Patent: Sep. 30, 2025

(54) RECYCLABLE CERAMIC CATALYST FILTER, FILTERING SYSTEM INCLUDING THE SAME, AND METHOD OF MANAGING THE FILTERING SYSTEM

(71) Applicant: Samsung Electronics Co., Ltd., Suwon-si (KR)

(72) Inventors: Hyukjae Kwon, Suwon-si (KR); Sangmin Ji, Suwon-si (KR); Jinkyu Kang, Suwon-si (KR); Kitae Park, Suwon-si (KR); Hyun Chul Lee, Suwon-si (KR); Seokwhan Chung, Suwon-si (KR); Hyoungwoo Choi, Suwon-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 0 days.

(21) Appl. No.: 17/966,369

(22) Filed: Oct. 14, 2022

(65) Prior Publication Data

US 2023/0031550 A1    Feb. 2, 2023

Related U.S. Application Data

(63) Continuation of application No. 17/038,105, filed on Sep. 30, 2020, now Pat. No. 11,491,475.

(30) Foreign Application Priority Data

Oct. 1, 2019    (KR) .................. 10-2019-0121746

(51) Int. Cl.
*A61L 9/20* (2006.01)
*B01D 53/86* (2006.01)
*B01D 53/88* (2006.01)
*B01D 53/96* (2006.01)
*B01J 35/00* (2006.01)
*B01J 35/04* (2006.01)
*B01J 35/39* (2024.01)
*B01J 35/56* (2024.01)
*B01J 38/48* (2006.01)

(52) U.S. Cl.
CPC ............ *B01J 35/56* (2024.01); *A61L 9/205* (2013.01); *B01D 53/8687* (2013.01); *B01D 53/885* (2013.01); *B01D 53/96* (2013.01); *B01J 35/19* (2024.01); *B01J 35/39* (2024.01); *B01J 38/48* (2013.01); *A61L 2209/14* (2013.01); *B01D 2255/802* (2013.01); *B01D 2255/9155* (2013.01); *B01D 2257/708* (2013.01)

(58) Field of Classification Search
CPC ...... B01J 35/04; B01J 35/0006; B01J 35/004; B01J 38/48; A61L 9/205; B01D 53/885; B01D 53/96; B01D 53/8687; B01D 2255/9155; B01D 2257/708; B01D 2255/802; B01D 46/2418; B01D 46/2476; B01D 46/785; B01D 2255/806
See application file for complete search history.

(56) References Cited

U.S. PATENT DOCUMENTS

| 7,607,294 | B2 | 10/2009 | Son | |
|---|---|---|---|---|
| 8,961,895 | B2 | 2/2015 | Freedman et al. | |
| 11,491,475 | B2 * | 11/2022 | Kwon | B01J 35/004 |
| 2001/0043890 | A1 * | 11/2001 | Son | F01N 3/2882 |
| | | | | 422/174 |
| 2004/0093861 | A1 * | 5/2004 | Watanabe | F01N 3/2006 |
| | | | | 60/311 |
| 2005/0042743 | A1 * | 2/2005 | Kawai | C09K 11/7704 |
| | | | | 257/40 |
| 2006/0127288 | A1 * | 6/2006 | Hay | A61L 9/014 |
| | | | | 422/186.3 |
| 2007/0070127 | A1 | 3/2007 | Lee et al. | |
| 2008/0072551 | A1 | 3/2008 | Zuberi | |
| 2009/0010801 | A1 | 1/2009 | Murphy et al. | |
| 2010/0058725 | A1 | 3/2010 | Konomi et al. | |
| 2014/0060400 | A1 | 3/2014 | Park et al. | |
| 2015/0064069 | A1 * | 3/2015 | Yi | A61L 9/20 |
| | | | | 422/121 |
| 2016/0303499 | A1 * | 10/2016 | Wiser | B03C 3/04 |
| 2018/0156089 | A1 * | 6/2018 | Mital | F01N 9/00 |

(Continued)

FOREIGN PATENT DOCUMENTS

| FR | 2 838 380 A1 * | 10/2003 | ............ A61L 9/205 |
|---|---|---|---|
| JP | 1993168855 A | 7/1993 | |
| JP | 2004169661 A | 6/2004 | |

(Continued)

OTHER PUBLICATIONS

Chinese Office Action dated Feb. 2, 2024, issued in corresponding Chinese Patent Application No. 202011048267.X (with translation) (20 pages).
Korean Office Action mailed Mar. 21, 2025 in KR Patent Application No. 10-2019-0121746, 27 pages (w/English- language translation).
Korean Office Action dated Apr. 7, 2025 issued in corresponding Korean Application No. 10-2020-0020546 (9 pages) (with translation).

*Primary Examiner* — Anthony J Zimmer
*Assistant Examiner* — Eric Scott Sherman
(74) *Attorney, Agent, or Firm* — CANTOR COLBURN LLP

(57) ABSTRACT

A recyclable ceramic catalyst filter, a filtering system including the same, and a method of managing the filtering system are provided. The ceramic catalyst filter has a monolithic structure including a first surface which blocks a first material; and a second surface which removes a second material that passed through the first surface, where the second surface is activated and operates as a catalyst layer which removes the second material in response to energy supplied to the second surface.

19 Claims, 20 Drawing Sheets

(56) References Cited

U.S. PATENT DOCUMENTS

2021/0023543 A1* 1/2021 Clowes .................. F01N 13/16

FOREIGN PATENT DOCUMENTS

| | | | | |
|---|---|---|---|---|
| JP | 2005125551 | A | 5/2005 | |
| JP | 2005201154 | A | 7/2005 | |
| JP | 2005248726 | * | 9/2005 | ............. B01D 39/14 |
| JP | 4345363 | B2 | 10/2009 | |
| KR | 100434940 | B1 | 6/2004 | |
| KR | 1020060115939 | A | 11/2006 | |
| KR | 1020120057056 | A | 6/2012 | |
| KR | 101339919 | B1 | 12/2013 | |
| KR | 101435587 | B1 | 8/2014 | |
| KR | 101436878 | B1 | 9/2014 | |
| KR | 1020150056498 | A | 5/2015 | |
| KR | 101956821 | B1 | 3/2019 | |
| KR | 1020190024390 | A | 3/2019 | |
| WO | WO 2016/066430 | A1 * | 5/2016 | ............. B01D 53/02 |
| WO | WO-2018123653 | A1 * | 7/2018 | ............. B01D 39/20 |

* cited by examiner

RECYCLABLE CERAMIC CATALYST FILTER, FILTERING SYSTEM INCLUDING THE SAME, AND METHOD OF MANAGING THE FILTERING SYSTEM

CROSS-REFERENCE TO RELATED APPLICATION

This application is a continuation of U.S. patent application Ser. No. 17/038,105, filed on Sep. 30, 2020, which claims priority to Korean Patent Application No. 10-2019-0121746, filed on Oct. 1, 2019, and all the benefits accruing therefrom under 35 U.S.C. § 119, the content of which in its entirety is herein incorporated by reference.

BACKGROUND

1. Field

The present disclosure relates to a filter, and more particularly, to a recyclable ceramic catalyst filter, a filtering system including the same, and a method of managing the filtering system.

2. Description of the Related Art

A Filter against fine dust is manufactured by using a melt blown technique, woven into glass fibers or plastics, or manufactured in a nonwoven form. Such a filter is classified and used for medium, high efficiency particulate air ("HEPA") or ultra low particulate air ("ULPA") according to their performance. Also, the filters filtrate a volatile organic compound ("VOC") along with fine dust particles through a deodorizing filter that adsorbs (deodorizes) the compound and particles by using carbon-based materials such as activated carbon. Currently, these filters are optionally used in air purifiers, thermal-exchange fans, or air conditioning systems in buildings. Although the performance varies depending on the filter, a HEPA filter exhibits excellent performance of filtering 0.3 micrometers (μm)-sized fine dust particles up to 99.97% by adsorption.

SUMMARY

Provided is a recyclable ceramic catalyst filter that is re-usable.

Provided is a ceramic catalyst filter that is capable of simultaneously filtrating a particle material and a gas material by using one filter.

Provided is a filtering system including the catalyst filter.

Provided is a method of managing the filtering system.

Additional aspects will be set forth in part in the description which follows and, in part, will be apparent from the description, or may be learned by practice of the presented embodiments.

According to an aspect of an embodiment, a catalyst filter includes a monolithic structure having a first surface which blocks a first material; and a second surface which removes a second material passing through the first surface, where the second surface is a part that is activated and functions as a catalyst layer which removes the second material in response to energy supplied to the second surface.

The monolithic structure may be porous. Also, an entirety of the monolithic structure may include the same catalyst material.

The first and second surfaces may each include surfaces that are vertically or horizontally parallel to each other with respect to a side of the catalyst filter through which the first and second materials enter.

The second surface may further include a second catalyst layer.

The monolithic structure may include a plurality of first grooves having an inlet at a side where the first and second materials enter; and a plurality of second grooves having an inlet at a side where the second material is discharged.

The first material may include micro-dust (e.g., fine dust), and the second material may include a volatile organic compound (VOC).

The catalyst material may be a photo-catalyst material. In this case, the second surface may be activated by an optical energy.

The catalyst material may be an electric catalyst material. In this case, the second surface may be activated by an electric energy. The catalyst material may be an ion catalyst material. In this case, the second surface may be activated by an ion energy. The catalyst material may be a thermal catalyst material. In this case, the second surface may be activated by a thermal energy. The catalyst material may be a metal compound.

The second catalyst layer may be a catalyst layer that is activated by a first type of energy different from a second type of the energy that is irradiated to the second surface.

A bottom surface of the second groove may be located between the inlets of the first grooves, and a bottom surface of the first groove may be located between the inlets of the second grooves. An inlet area of the first groove and a bottom area of the second groove may be different from each other. An air-permeability of the bottom surface of the first groove and an air-permeability of the bottom surface of the second groove may be different from each other. A bottom surface of the first groove may have a configuration that blocks the second material. An area of the inlet of the second groove may be larger than an area of the bottom surface of the first groove. An area of the inlet of the second groove and an area of the bottom surface of the first groove may be the same. A diameter of the first groove may decrease toward the bottom surface from the inlet of the first groove. A diameter of the second groove may decrease toward the bottom surface from the inlet of the second groove. A wall between the first groove and the second groove may have an air-permeability and allow the second material to penetrate through the wall. The first and second grooves may each be in the form of a wedge. The air-permeability may be uniform throughout an entirety of the wall or may differ along a predetermined direction in the wall.

According to an aspect of another embodiment, a filtering system including a recyclable ceramic catalyst filter includes the recyclable ceramic catalyst filter according to an embodiment and an energy supply device which supplies energy for catalyst activation of the catalyst filter.

The energy supply device may include an optical energy source, an electric energy source, an ion energy source, or a thermal energy source.

The energy supply device may be formed to supply two types of energies selected from an optical energy, an electric energy, an ion energy, and a thermal energy.

According to an aspect of another embodiment, a method of managing a filtering system includes: activating one surface of the catalyst filter to a catalyst layer to operate as a catalyst layer; separating and washing the catalyst filter based on determination that the catalyst filter reaches a first condition; and disposing the washed catalyst filter to the original location.

The activating of the one surface of the catalyst filter may include supplying energy to the one surface. The first condition may include a condition that a pressure difference in predetermined two points of the catalyst filter is at least 250 about pascals (Pa). The supplying of the energy to the one surface may include one or two processes selected from: supplying an optical energy to the one surface; supplying an electric energy to the one surface; supplying an ion energy to the one surface; and supplying a thermal energy to the one surface.

In one embodiment, the second catalyst layer may be further included on the one surface. Here, the second catalyst layer may be activated by using a method different from that activating the one surface of the catalyst filter.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
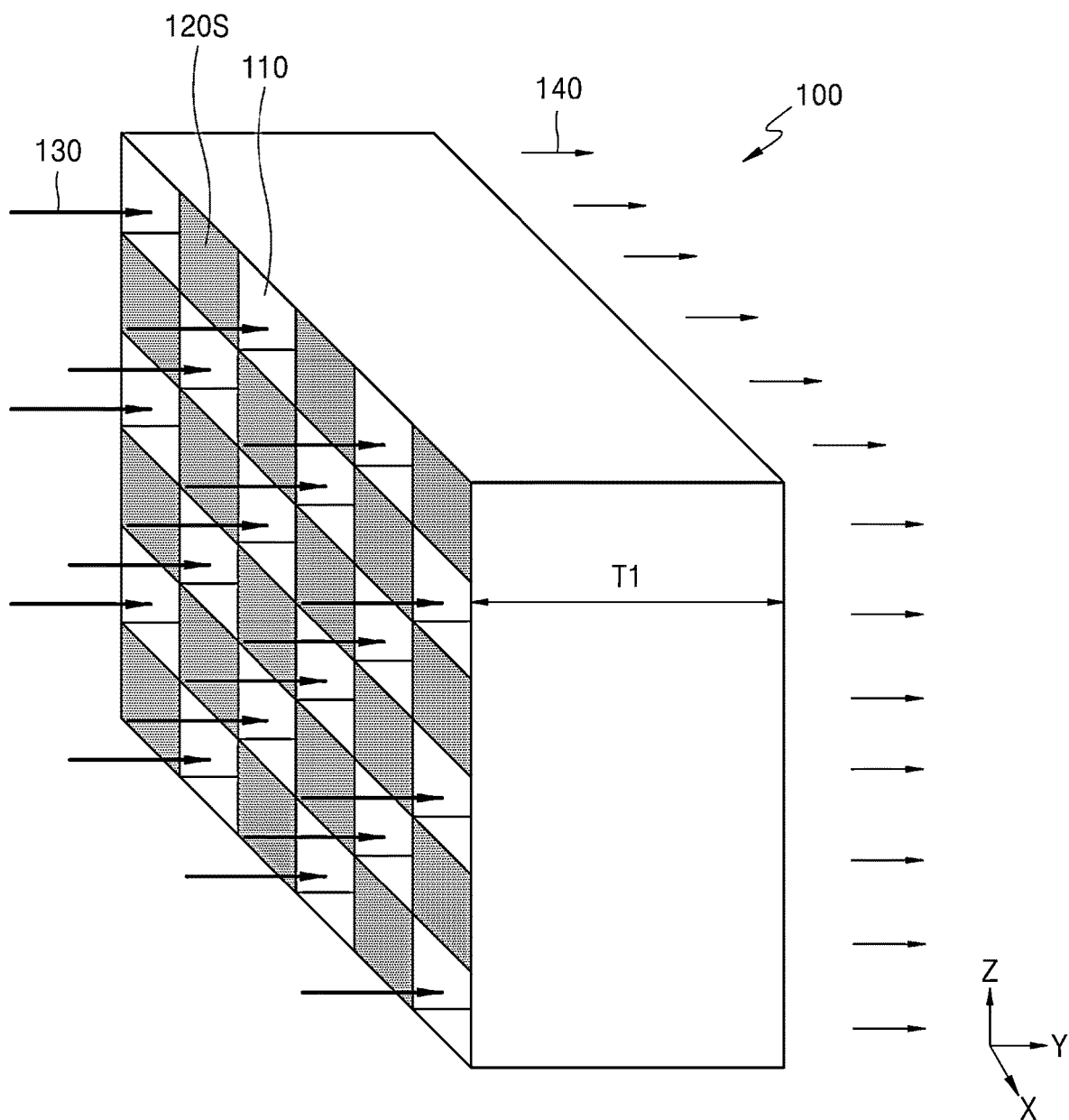
FIG. 1 is a front perspective view of a ceramic catalyst filter (a first catalyst filter) according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. The terminology used herein is for the purpose of describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an." "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. It will be understood that when an element is referred to as being "on" another element, it can be directly on the other element or intervening elements may be present therebetween. In contrast, when an element is referred to as being "directly on" another element, there are no intervening elements present. It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Hereinafter, a recyclable ceramic catalyst filter according to an embodiment, a filtering system including the same, and a method of managing the filtering system will be described in detail with reference to the attached drawings. In the drawings, the thickness of layers or regions may be exaggerated for clarity.

Here, catalyst filters used herein may be one possible means for purifying air. Also, the catalyst filters used herein may one of members filtering or removing materials that are noxious or can be harmful to humans from air. The catalyst filters used herein may be one of members discharging relatively clean material, for example, fluid than that on the side of an inlet. The material may be a gas including particles or particulate components.

First, a recyclable ceramic catalyst filter (also, referred to as "first catalyst filter") will be described.

Referring to FIG. 1, a first catalyst filter 100 includes an air inlet surface through which a material 130 enters and a gas discharge surface through which a gas 140 is discharged. The discharge surface is opposite to the inlet surface in Y-axis direction. The material 130 may include at least two materials that need to be filtered or removed. For example, the material 130 may include a particulate first material and a gaseous second material. The first catalyst filter 100 may have a predetermined thickness T1 in a direction (i.e., Y-axis direction). Y-axis direction is a direction to which the gas 140 generated as a result of a catalyst reaction between the first catalyst filter 100 and a part of the material 130 is discharged. The first catalyst filter 100 defines a plurality of first grooves 110. Each of the first grooves 110 has an inlet at a side (i.e., the inlet surface) where the material 130 enters and a bottom surface 110B (see FIG. 4) at a side opposite to the inlet in the Y-axis direction. Here, the bottom surface of the groove is defined as an inner end of the groove opposite to an open end of the groove. The material 130 enters the first catalyst filter 100 through the inlets of the plurality of first grooves 110. The plurality of first grooves 110 is arranged at regular intervals. The plurality of first grooves 110 may be arranged in parallel to each other. The first catalyst filter 100 includes a plurality of first surfaces 120S at a side (i.e., the air inlet surface) where the material 130 enters. The plurality of first surfaces 120S is arranged at regular intervals. The first surfaces 120S are arranged between the first grooves 110. That is, the first surfaces 120S and the first grooves 110 are alternatively arranged in both horizontal (i.e., X-axis direction) and vertical (i.e., Z-axis direction) directions as shown in FIG. 2. One of the first grooves 110 may be surrounded by four first surfaces 120S, and one of the first surfaces 120S may be surrounded by four first grooves 110.

Figure 2A:
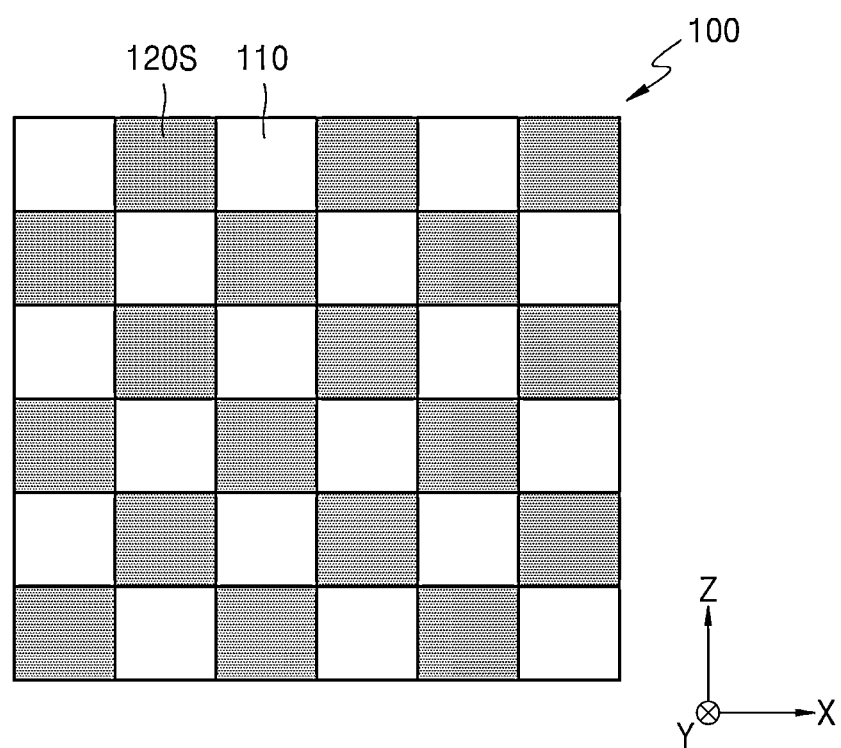
FIG. 2A is a front view (view from an air inlet surface) of an embodiment of the ceramic catalyst filter of FIG. 1.
Figure 2B:
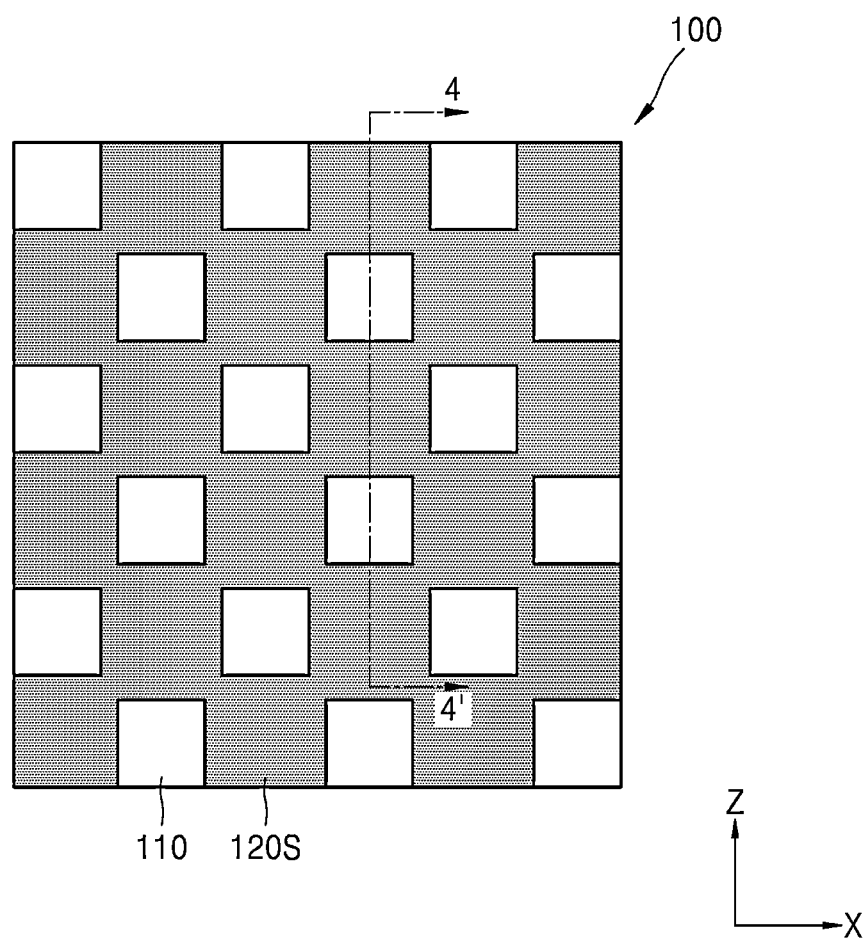
FIG. 2B is another front view of the ceramic catalyst filter of FIG. 1, emphasizing thickness of side walls.

FIG. 2A is a front view of an embodiment of the first catalyst filter 100 of FIG. 1. That is, FIG. 2A is a view from an air inlet surface of the first catalyst filter 100. FIG. 2B is another front view of the ceramic catalyst filter of FIG. 1, exaggerating the thickness of the side walls of the first grooves 110 for clarity.

Figure 3:
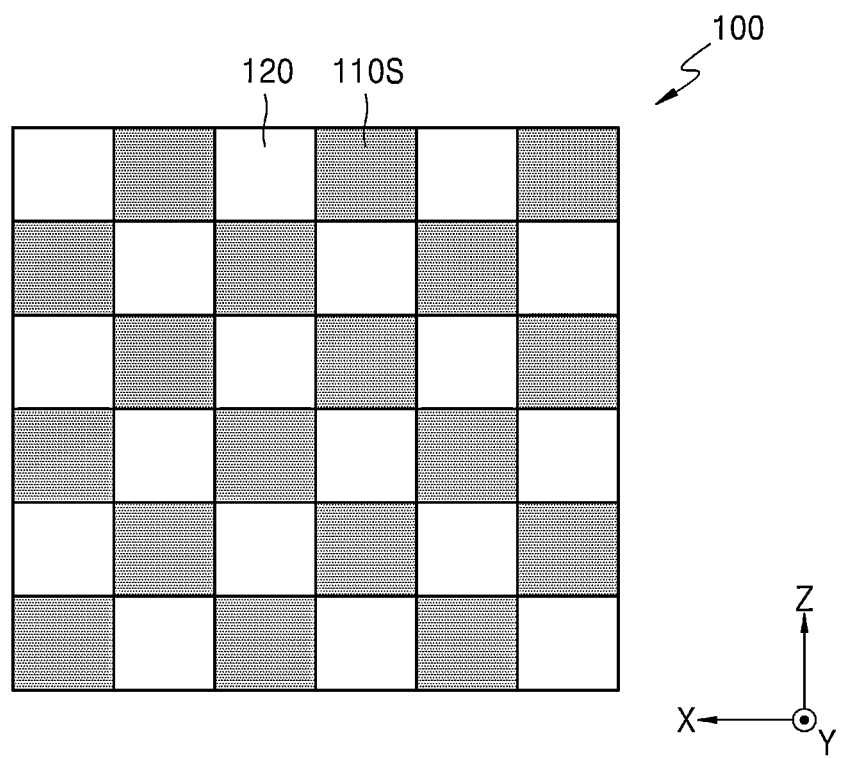
FIG. 3 is a rear view (view from a gas discharge surface) of an embodiment of the ceramic catalyst filter of FIG. 1.

FIG. 3 shows an embodiment of a back surface, that is, a gas discharge surface of the first catalyst filter 100.

Referring to FIG. 3, the first catalyst filter 100 includes a plurality of second grooves 120 and a plurality of second surfaces 110S at a side (i.e., the gas discharge surface) where a gas is discharged. The plurality of second grooves 120 may be an outlet, that is, a discharge port through which a gas flows out. The gas discharged through the plurality of second grooves 120 may be a relatively clean or innoxious gas as a product of filtering a harmful material or impurities from the material 130 that enters through the plurality of first grooves 110 or may include this gas and the air. The plurality of second grooves is arranged at regular intervals. The plurality of second surfaces 110S is also arranged at regular intervals. An arrangement relation between the plurality of second grooves 120 and the plurality of second surfaces 110S may follow an arrangement relation between the plurality of first grooves 110 and the plurality of first surfaces 120S. The plurality of second surfaces 110S corresponds to the first grooves 110, and the plurality of second grooves 120 corresponds to the plurality of first surfaces 120S.

Figure 4:
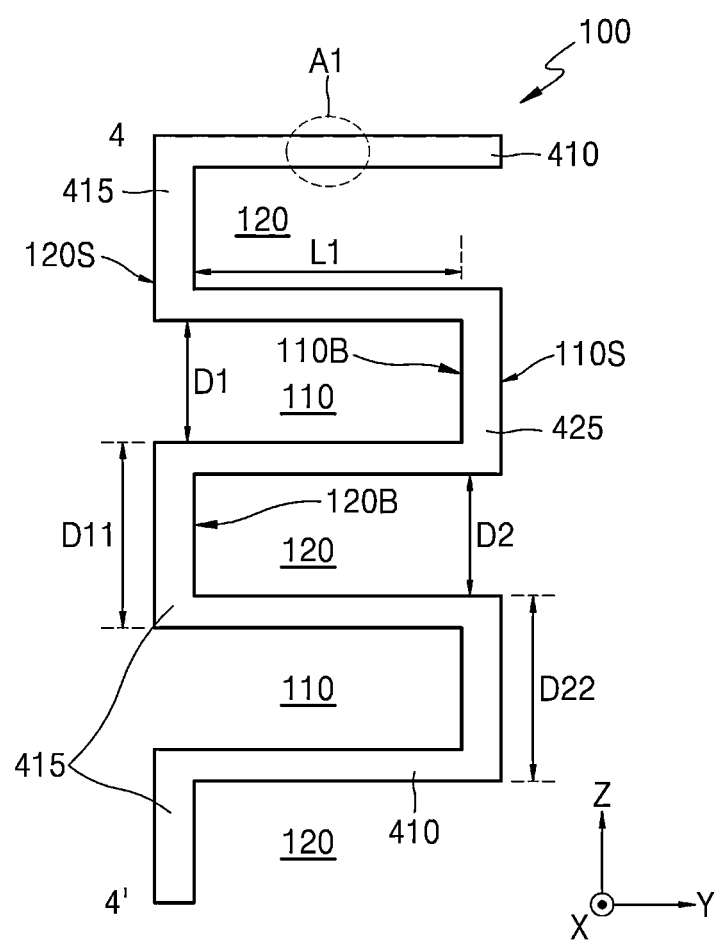
FIG. 4 is a cross-sectional view taken along line 4-4' of FIG. 2.

FIG. 4 is a cross-sectional view of FIG. 2B taken along line 4-4'.

The first catalyst filter 100 may be a monolithic structure or a single body frame. The first catalyst filter 100 as a whole may have a frame formed of or include the same material (e.g., a catalyst material). The first catalyst filter 100 is a single body but will be divided into a horizontal part and a vertical part for convenience of description.

Referring to FIG. 4, the first catalyst filter 100 may be a structure having a frame in which the plurality of first and second grooves 110 and 120 is stacked in a Z-axis direction.

Particularly, the first catalyst filter 100 includes a plurality of horizontal parts 410 and a plurality of vertical parts 415 and 425. The horizontal parts 410 are spaced apart from each other in the Z-axis direction. Here, the Z-axis direction will be referred to as a vertical direction for convenience of description. The horizontal parts 410 are parallel to each other in a Y-axis direction. A length of each of the plurality of horizontal parts 410 in the Y-axis direction may be the same. The Y-axis direction may be a direction in which the resulting gas 140 produced as a result of a catalyst reaction is discharged from the first catalyst filter 100. The Y-axis direction is perpendicular to the Z-axis direction. Here, for convenience of description, the Y-axis direction is considered as a horizontal direction. The vertical parts 415 and 425 are parallel to each other and are spaced apart from each other in the Z-axis direction. The vertical parts 415 and 425 are arranged between the horizontal parts 410, alternately. The horizontal parts 410 are also alternately arranged between the vertical parts 415 and 425. The horizontal parts 410 are connected to each other through the vertical parts 415 or 425 The vertical parts 415 and 425 are connected to each other through the horizontal parts 410. The plurality of vertical parts 415 and 425 includes a plurality of first vertical parts 415 and a plurality of second vertical parts 425. The plurality of first vertical parts 415 and the plurality of second vertical parts 425 are spaced apart from each other in the Y-axis direction. The first vertical parts 415 are spaced apart from each other in the Z-axis direction and are aligned side-by-side in the Z-axis direction. The second vertical parts 425 are also spaced apart from each other in the Z-axis direction and are aligned side-by-side in the Z-axis direction. The plurality of first vertical parts 415 is located at a side (i.e., the air inlet surface) where the material 130 enters. The plurality of second vertical parts 425 is located at a side (i.e., the gas discharge surface) where the gas 140 produced by the catalyst reaction is discharged.

The plurality of horizontal parts 410 may be walls of the first and second grooves 110 and 120. That is, the horizontal parts 410 are each located between the first groove 110 and the second groove 120 and thus become a boundary of each of the first and second grooves 110 and 120. The walls denote side walls of the first and second grooves 110 and 120. Thicknesses of the horizontal parts 410 in the Z-axis direction may be the same or may be different from each other in some portions. The thickness of each of the plurality of horizontal parts 410 may be the same with thickness of each of the plurality of vertical parts 415 and 425 or may be different from the thicknesses of the plurality of vertical parts 415 and 425. The horizontal parts 410 which become the side walls of the first grooves 110 are spaced apart from each other at a first distance D1 in the Z-axis direction. The first distance D1 may be a diameter of an inlet of the first groove 110. The horizontal parts 410 which become the side walls of the second grooves 120 are spaced apart from each other by a second distance D2 in the Z-axis direction. The second distance D2 may be a diameter of an inlet of the second groove 120. In one embodiment, the first and second distances D1 and D2 may be the same. That is, diameters of inlets of the first and second grooves 110 and 120 may be the same. Y-axis lengths L1 of the plurality of horizontal parts 410 may be the same. Depths of the first and second grooves 110 and 120 in the Y-axis direction may be determined by the Y-axis lengths L1 of the horizontal parts 410. Therefore, the depths of the first and second grooves 110 and 120 may be the same. In some embodiments, the depth of the first groove 110 and the depth of the second groove 120 may be different from each other. Inner parts of the plurality of first vertical parts 415 may be bottom surfaces 120B of the second grooves 120. Inner parts of the plurality of second vertical parts 425 may be bottom surfaces 110B of the first grooves 110. An air permeability of the bottom surfaces 110B of the first grooves 110 and an air permeability of the bottom surfaces 120B of the second grooves 120 may be different from each other. The bottom surfaces 120B of the second grooves 120 may have a configuration that blocks a gaseous material. A diameter D11 of the first vertical part 415 and a diameter D22 of the second vertical part 425 may be the same. Y-axis direction thicknesses of the first and second vertical parts 415 and 425 may be the same. The diameter D11 of the first vertical part 415 may be greater than the second distance D2, and the diameter D22 of the second vertical part 425 may be greater than the first distance D1.

In a case that the thickness of the horizontal part 410 in the Z-axis direction is negligible compared to the first and second distances D1 and D2, as shown in FIGS. 2A, a size (i.e., area in a plane defined by the X-axis direction and the Z-axis direction) of the inlet of the first groove 110 and a size of the first surface 120S between the first grooves 110 may be substantially the same. Also, a size of the inlet of the second groove 120 and a size of the second surface 110S between the second grooves 120 may be substantially the same. That is, the first groove 110 and the first surface 120S may be substantially symmetrical to each other, and the second groove 120 and the second surface 110S may be substantially symmetrical to each other in their shapes in a front view.

On the other hand, in a case that the thickness of the horizontal part 410 in the Z-axis direction is not negligible compared to the first and second distances D1 and D2, as shown in FIGS. 2B and 4, when the size of the inlet of the first groove 110 is the same as the size of the bottom surface 120B of the second groove 120, the size of the inlet of the first groove 110 may be smaller than the size of the first surface 120S. When the size of the inlet of the second groove 120 is the same as the size of the bottom surfaces 110B of the first groove 110, the size of inlet of the second groove 120 may be smaller than that of the second surface 110S.

The plurality of horizontal parts 410 and the plurality of vertical parts 415 and 425 are connected to form a single body which may be a material layer of ceramic type formed of or include the same catalyst material. The catalyst material may vary according to a type of energy supplied to the first catalyst filter 100 for activation of the catalyst material.

In one embodiment, when the energy supplied to the first catalyst filter 100 is an optical energy, the catalyst material may be a metal compound that may generate a photo-catalyst reaction, and examples of the metal compound may be $TiO_2$ or $WO_3$. The photo energy may include ultraviolet energy or visible light energy.

In another embodiment, when the energy supplied to the first catalyst filter 100 is an electric energy of direct current ("DC") or alternating current ("AC"), the catalyst material may be a metal compound that allows an oxygen reduction reaction ("ORR") of an electric conductivity at the plurality of horizontal parts 410 and the plurality of vertical parts 415 and 425. Here, the metal compound may be a compound containing a metal such as cobalt, nickel, or manganese or may include a noble metal oxide.

In other embodiments, when the energy supplied to the first catalyst filter 100 is an ion energy, the catalyst material may be a metal compound that allows ozone oxidation, and examples of the metal compound may include $MnO_2$ or $ZnO_2$. For example, the ion energy may be a plasma energy.

In some embodiments, when the energy supplied to the first catalyst filter 100 is a thermal energy, the catalyst material may be a metal compound that allows a low-temperature oxidation reaction. In one embodiment, the metal compound may be a compound containing Cu, Co, Ni, Fe, Al, Si, or a noble metal. The low-temperature oxidation reaction denotes an oxidation reaction that occurs in a temperature range of room temperature to 100 degrees Celsius (° C.). For example, the thermal energy may include an infrared energy or an energy supplied from a heat source such as a heater.

At least the horizontal parts 410 are activated by the energy supplied to the first catalyst filter 100, and a part of the whole vertical parts 415 and 425 may further be activated. As a result, a part (region) of the first catalyst filter 100 to which the energy is supplied may become a catalyst layer or may serve as a catalyst layer. The energy may be supplied to side walls or a bottom surface of the second groove 120. A gas component included in the material 130 may generate a catalyst reaction (e.g., by reacting with oxygen when an optical energy is supplied to the material 130) while passing through the catalyst layer and may be decomposed. The gas component may be a volatile organic compound ("VOC") or anther harmful gas. Examples of the VOC may be formaldehyde, acetaldehyde, ammonia, toluene, or acetic acid.

Figure 5:
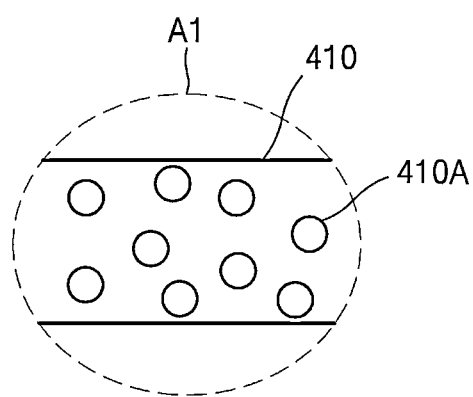
FIGS. 5 and 6 are enlarged cross-sectional views of embodiments of a first part A1 of FIG. 4.

FIG. 5 is an enlarged view of an embodiment of a first part A1 of the horizontal part 410 in FIG. 4.

Referring to FIG. 5, the horizontal part 410 defines pores 410A. In one embodiment, the vertical parts 415 and 425 may not define pores.

In another embodiment, the vertical parts 415 and 425 may define pores, but a pore density of the vertical parts 415 and 425 may be lower than that of the horizontal parts 410.

In other embodiments, the first vertical parts 415 may define pores, and the second vertical parts 425 may not define pores.

In some embodiments, the first and second vertical parts 415 and 425 may define pores, and a pore density of the second vertical parts 425 may be lower than that of the first vertical parts 415. Due to the different pore density, air permeabilities of the first vertical parts 415 and the second vertical parts 425 may be different from each other.

Figure 6:
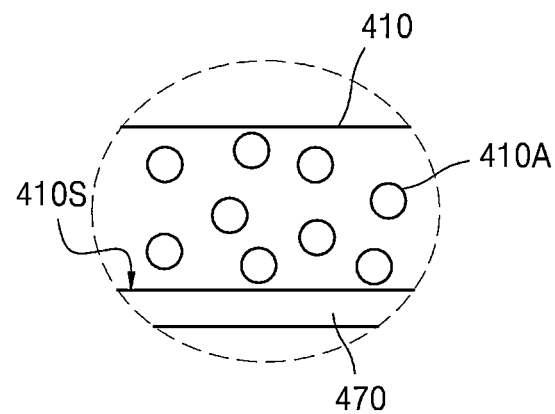

FIG. 6 is an enlarged view of another embodiment of the first part A1 of the horizontal part 410 of FIG. 4.

Referring to FIG. 6, the horizontal part 410 may define pores 410A. A first catalyst layer 470 is disposed on a surface 410S of the horizontal part 410 to which energy is supplied. The first catalyst layer 470 covering the surface 410S is a material layer that is formed separately from the horizontal part 410 and may be different from the material of the horizontal part 410. For example, when the horizontal part 410 is formed of or include a first catalyst material, the first catalyst layer 470 may be formed of or include a second catalyst material that is different from the first catalyst material in the content of the material. In one embodiment, when the horizontal part 410 is a catalyst material that may be activated by a certain type of energy (e.g., a thermal energy) selected from the four types of energies described above, the first catalyst layer 470 may be formed of or include a catalyst material that may be activated by another type of energy (e.g., an optical energy) of the four types of energies that is different from the selected energy activating the horizontal part 410. In other words, the type of energy activating the horizontal part 410 and the type of energy activating the first catalyst layer 470 may be different from each other. Therefore, when the first catalyst layer 470 is provided, two different types of energies may be supplied simultaneously to the first catalyst filter 100.

Figure 7:
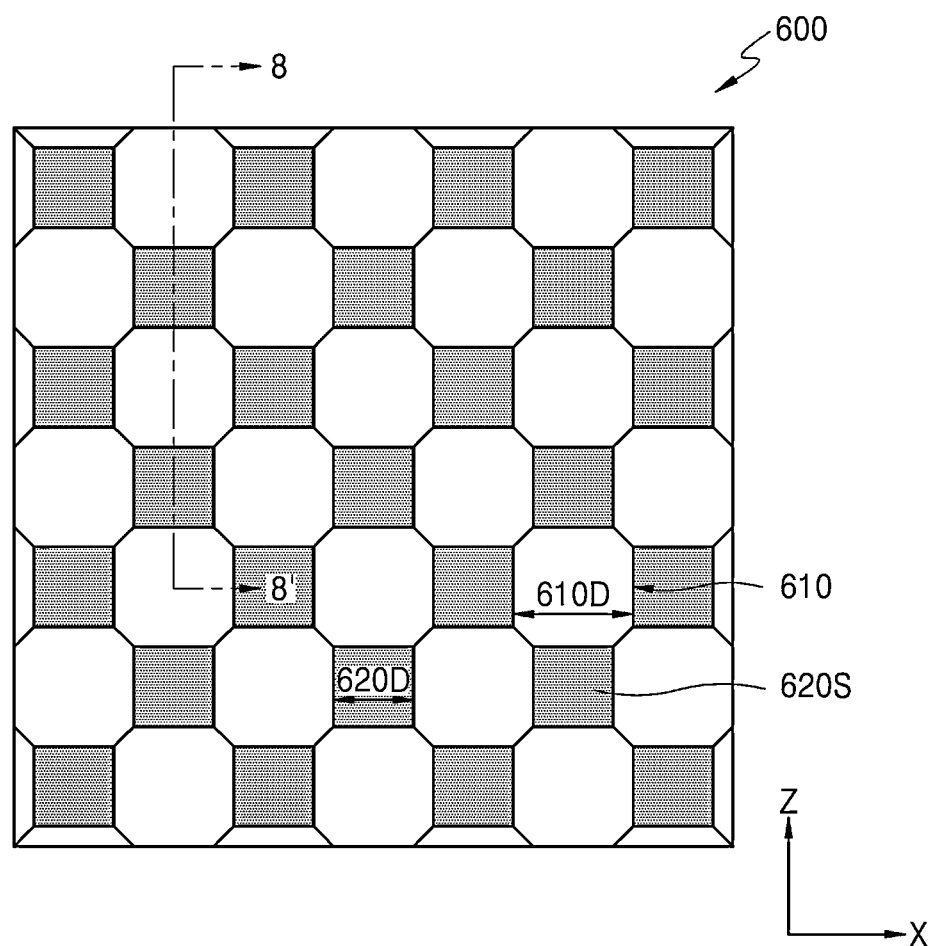
FIG. 7 is a front view of an air inlet surface of a ceramic catalyst filter (a second catalyst filter) according to another embodiment.

FIG. 7 shows a recyclable ceramic catalyst filter 600 (hereinafter, also referred to as "a second catalyst filter 600") according to another embodiment.

Referring to FIG. 7, a second catalyst filter 600 includes a plurality of first grooves 610 and a plurality of first surfaces 620S. Air entering the second catalyst filter 600 is discharged through the second grooves 615. The first grooves 610 are arranged at regular intervals. The first grooves 610 are horizontally and vertically spaced apart from each other. The first surfaces 620S are each located between the first grooves 610. Four first surfaces 620S are arranged around one first groove 610. Four first grooves 610 are arranged around one first surface 620S. The first surfaces 620S are arranged at a regular interval. The first surfaces 620S are horizontally and vertically spaced apart from each other. The first grooves 610 contact each other in a diagonal direction (i.e., direction perpendicular to the Y-axis direction and inclined to the X-axis direction and the Z-axis direction), but the first surfaces 620S are spaced apart from each other in the diagonal direction. A size of the inlet of the first groove 610 is larger than that of the first surface 620S. A diameter 610D of an inlet of the first groove 610 is larger than a diameter 620D of the first surface 620S. Therefore, the first groove 610 and the first surface 620S are asymmetrical to each other. A shape of the first groove 610 and a shape of the first surface 620S may be different from each other. Each of the first grooves 610 may have an overall square shape, specifically a square with four chamfered corners in a front view. In other words, the shape of the first grooves 610 in the front view is an octagon in which a length of every other side is shorter than a length of each of the other sides. The first surface 620S is a square.

Figure 8:
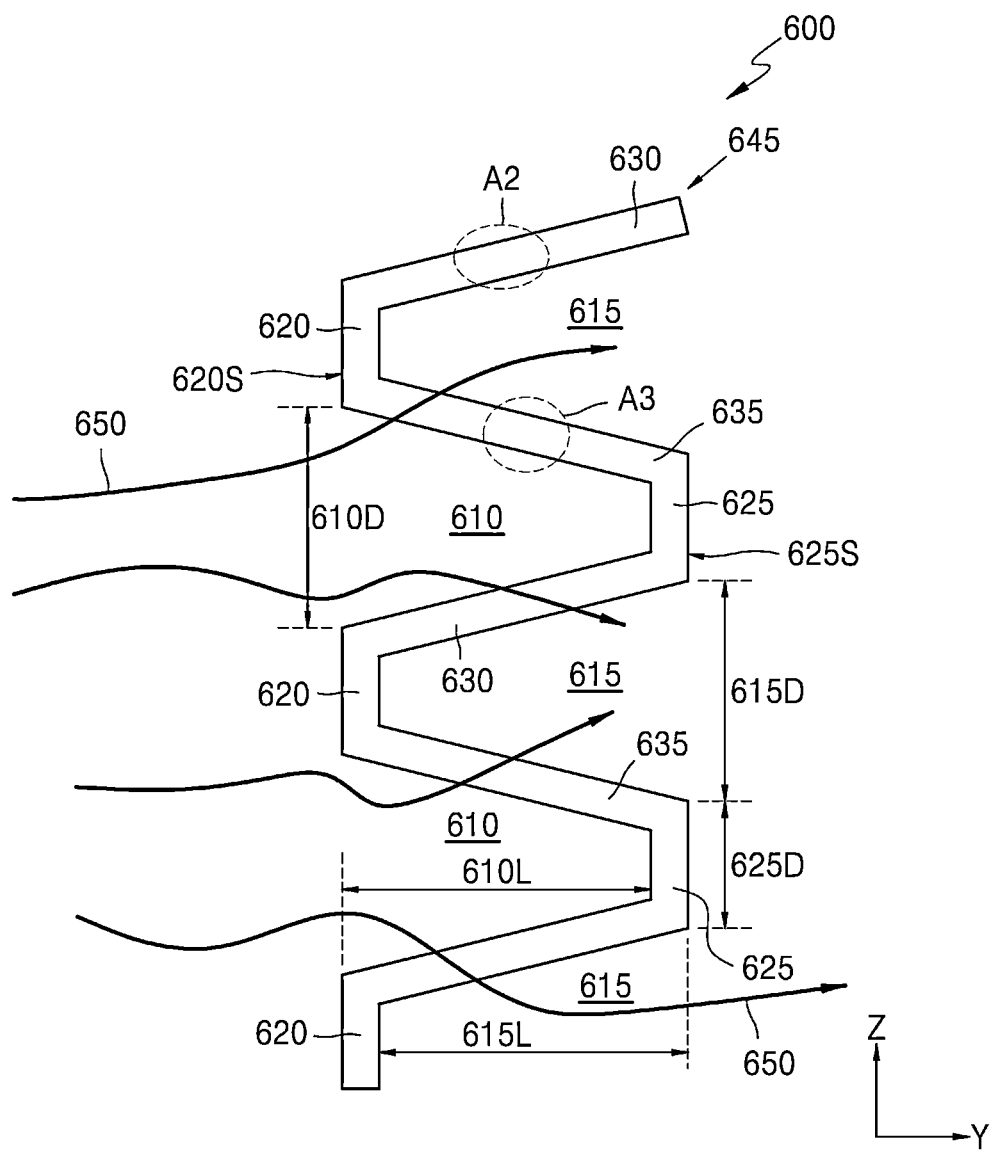
FIG. 8 is a cross-sectional view taken along line 8-8' of FIG. 7.

FIG. 8 is a cross-sectional view of the second catalyst filter 600 of FIG. 7 taken along line 8-8'.

Referring to FIG. 8, the second catalyst filter 600 includes the plurality of first grooves 610 that are sequentially stacked in the Z-axis direction. Also, the second catalyst filter 600 includes a plurality of second grooves 615 that are sequentially stacked in the Z-axis direction. The plurality of first grooves 610 and the plurality of second grooves 615 are alternatively stacked in the Z-axis direction. The plurality of first grooves 610 and the plurality of second grooves 615 are formed in directions opposite to each other. That is, inlets of the plurality of first grooves 610 and inlets of the plurality of second grooves 615 face opposite directions from each other. The inlets of the first grooves 610 face a (−) direction of the Y-axis, which is a direction in which air 650 enters. On the other hand, the inlets of the second grooves 615 face a (+) direction of the Y-axis, which is a direction in which air 650 flows out. A diameter of the first groove 610 decreases along the (+) direction of the Y-axis. Whereas, a diameter of the second groove 615 increases along the (+) direction of the Y-axis. A diameter 615D of the inlet of the second groove 615 and a diameter 610D of the inlet of the first groove 610 may be the same or different from each other. A length 610L of the first groove 610 and a length 615L of the second groove 615 may be the same or different from each other. The plurality of first grooves 610 and the plurality of second grooves 615 are divided by a single body frame 645. That is, the single body frame 645 exists between the first grooves 610 and the second grooves 615. The single body frame 645 may be formed of or include the same material of the first catalyst filter 100. The single body frame 645 includes a plurality of vertical parts 620 and 625 and a plurality of inclined parts 630 and 635. The parts 620, 625, 630, and 635 are connected to each other and thus form a continuous (i.e., monolithic) body. Therefore, there is no boundary between the parts 620, 625, 630, and 635. The plurality of vertical parts 620 and 625 exists between the plurality of inclined parts 630 and 635. The plurality of inclined parts 630 and 635 is disposed between the plurality of vertical parts 620 and 625. The vertical parts 620 and 625 are parallel to the Z-axis direction. The vertical parts 620 are spaced apart in the Z-axis direction. The vertical parts 625 are spaced apart in the Z-axis direction. The first vertical part 620 and the second vertical parts 625 are spaced apart from each other in the Y-axis direction. The inclined parts 630 and 635 are also spaced apart from each other in the Z-axis direction. The plurality of second vertical parts 625 becomes bottoms of the first grooves 610. The plurality of first vertical parts 620 becomes bottoms of the second grooves 615. An air permeability of the bottoms of the first grooves 610 and an air permeability of the bottoms of the second grooves 615 may be different from each other. The bottoms of the second grooves 615 may block a flow of a gaseous material. A plurality of first surfaces 620S at an air-entering side of the plurality of first vertical parts 620 is parallel to a plurality of second surfaces 625S of the plurality of second vertical parts 625 in the Z-axis direction. A size of the first surface 620S and a size of the second surface 625S may be the same.

The plurality of inclined parts 630 and 635 may include a plurality of first inclined parts 630 having a positive slope and a plurality of second inclined parts 635 having a negative slope with respect to the Y-axis. The first inclined parts 630 are parallel to each other and are spaced apart from each other. The second inclined parts 635 are also parallel to each other and are spaced apart from each other. The first inclined part 630 and the second inclined part 635 may be symmetrical with respect to the Y-axis. The first inclined parts 630 and the second inclined parts 635 are inclined side walls of the first grooves 610. Also, the first inclined parts 630 and the second inclined parts 635 are inclined side walls of the second grooves 615. A distance between the first inclined part 630 and the second inclined part 635 that form side walls of the first groove 610 decreases along the (+) direction of the Y-axis. A distance between the first inclined part 630 and the second inclined part 635 that form side walls of the second groove 615 decreases along the (+) direction of the Y-axis. The first and second vertical parts 620 and 625 and the second inclined part 635 exist between the plurality of first inclined parts 630.

Configurations of a second part A2 and a third part A3 of the single body frame 645 may be the same with the first part A1 shown in FIG. 5 or FIG. 6. That is, the plurality of first inclined parts 630 and the plurality of second inclined parts 635 may include pores. Also, a separate catalyst layer may be further prepared on surfaces of the plurality of first and second inclined parts 630 and 635 through which air flows out, i.e., on side walls and bottoms of the second grooves 615. A material of the prepared catalyst layer may be different from the material of the single body frame 645. Regarding a shape of the single body frame 645, the single body frame 645 may include a plurality of parts projecting in the (+) direction of the Y-axis or may include a plurality of parts projecting in the (−) direction of the Y-axis.

Figure 9:
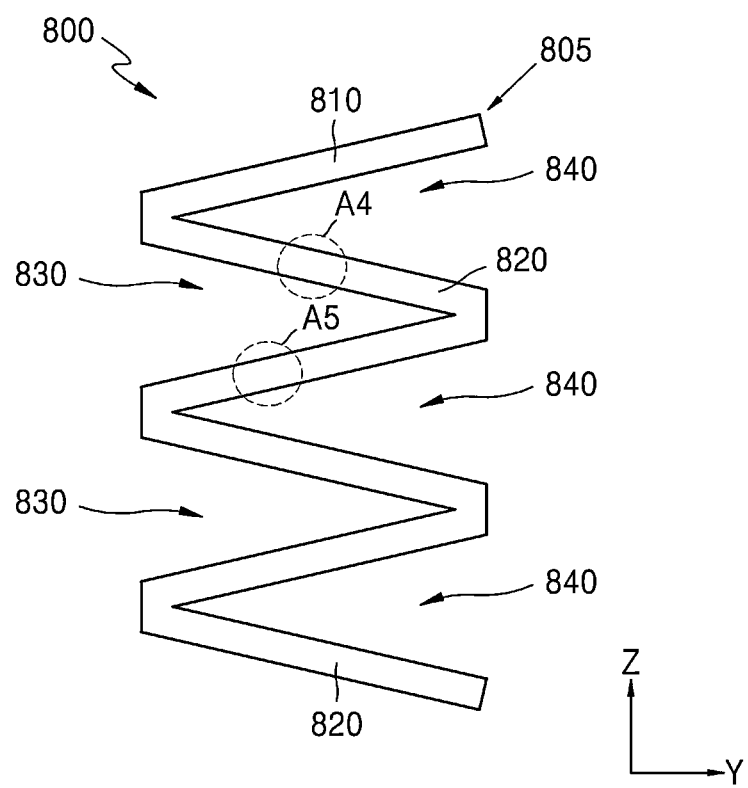
FIG. 9 is a cross-sectional view of a modified example of FIG. 8, showing a ceramic catalyst filter according to another embodiment.

FIG. 9 shows a recyclable ceramic catalyst filter 800 (hereinafter, also referred to as "a third catalyst filter 800") according to another embodiment.

FIG. 9 is a modified example of the second catalyst filter 600 of FIG. 8.

Referring to FIG. 9, the third catalyst filter 800 includes a single body frame 805 and includes a plurality of first grooves 830 and a plurality of second grooves 840 that are defined by the single body frame 805. A shape of the single body frame 805 may be the same with that of the single body frame 645 of FIG. 8 except for the plurality of vertical parts 620 and 625. That is, the single body frame 805 may include a plurality of first inclined parts 810 and a plurality of second inclined parts 820 and does not include vertical parts that connect the first and second inclined parts 810 and 820. In the single body frame 805, one end of the first inclined part 810 and one end of the second inclined part 820 are connected directly, and the other end of the first inclined part 810 and the other end of the second inclined part 820 are spaced apart from each other. A distance between the first and second inclined parts 810 and 820 that form inclined side walls of the first groove 830 decreases further along the (+) direction of the Y-axis. As a result, a diameter of the first groove 830 in the front view decreases further along the (+) direction of the Y-axis, and thus a shape of the first groove 830 is a wedge. Inclined side walls of the second groove 840 consist of the first and second inclined parts 810 and 820, where one end of the first inclined part 810 and one end of the second inclined part 820 are connected directly, and the other end of the first inclined part 810 and the other end of the second inclined part 820 are spaced apart from each other. A distance between the first and second inclined parts 810 and 820 that form the inclined side walls of the second groove 840 increases further along the (+) direction of the Y-axis. Accordingly, a diameter of the second groove 840 increases further along the (+) direction of the Y-axis. Therefore, a shape of the second groove 840 is also a wedge, but a direction of the wedge is direct opposite from that of the first groove 830.

The third catalyst filter 800 may be the same as the second catalyst filter 600 of FIG. 7, except that the vertical parts 620 and 625 of the single body frame 645 are removed from the second catalyst filter 600 and that parts of the inclined parts 630 and 635 which would be connected to the vertical parts 620 and 625 in FIG. 7 are directly connected to each other.

In FIG. 9, a size of an inlet of the first groove 830 at a side where air enters may be the same with a size of an inlet of the second groove 840 at a side through which the air is discharged. However, in some embodiments, a size of an inlet of the first groove 830 and a size of an inlet of the second groove 840 may be different from each other. Configurations of a fourth part A4 and a fifth part A5 of the single body frame 805 may be the same as the first part A1 shown in FIG. 5 or FIG. 6. That is, the plurality of first inclined parts 810 and the plurality of second inclined parts 820 may include pores 410A. Also, a separate catalyst layer may be further prepared on surfaces of the plurality of first and second inclined parts 810 and 820 through which air flows out, i.e., on side walls of the second grooves 840. Here, a material of the prepared catalyst layer may be different from the material of the single body frame 805.

Figure 10:
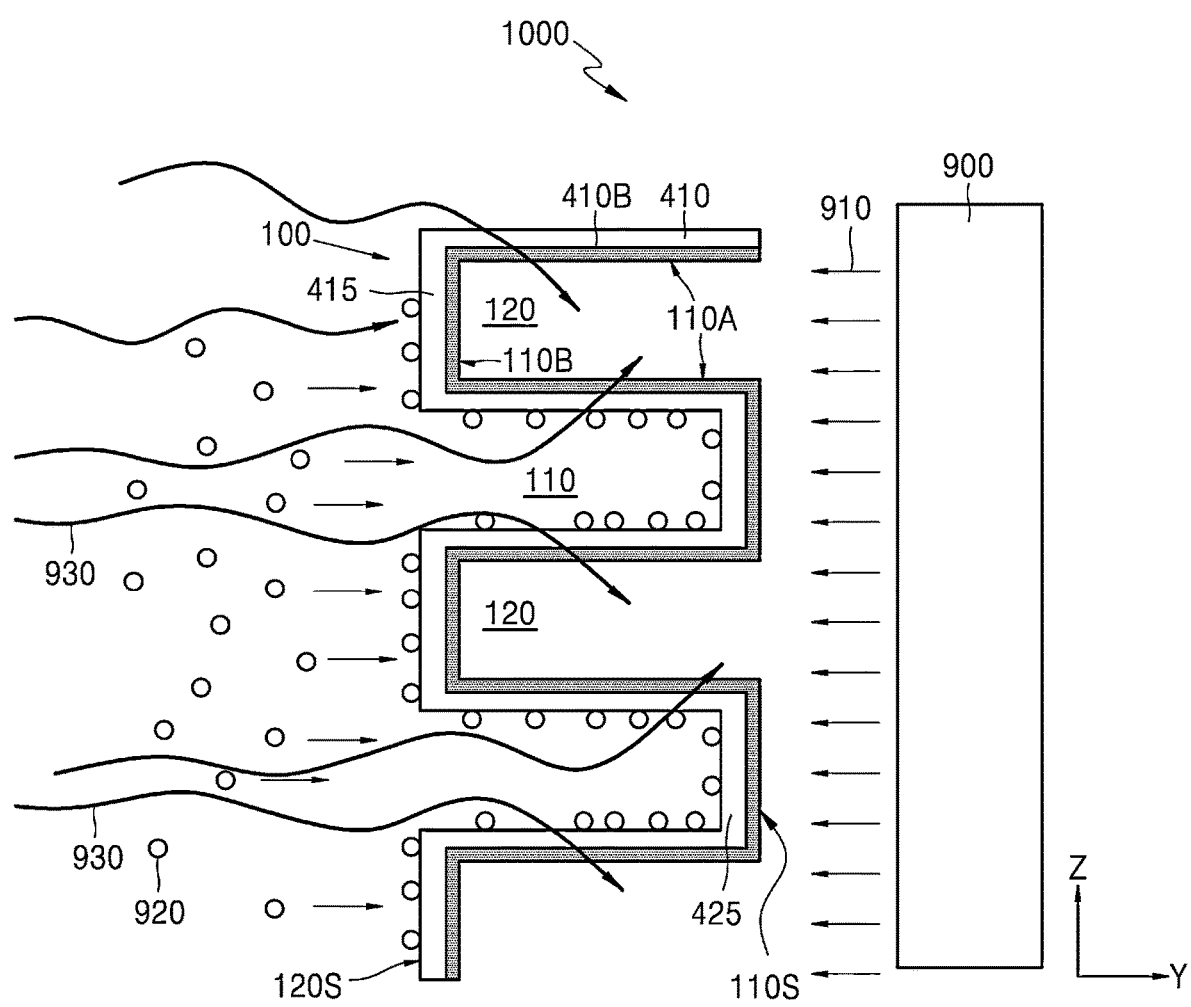
FIG. 10 is a cross-sectional view of a filtering system including the ceramic catalyst filter according to an embodiment.

FIG. 10 shows a first filtering system 1000 including the recyclable ceramic catalyst filter, according to an embodiment.

Referring to FIG. 10, the first filtering system 1000 includes a first catalyst filter 100 and an energy supply device 900. The energy supply device 900 generates an energy 910 that activates a surface of the first catalyst filter 100 through which air is discharged, i.e., a surface that is directly exposed to the energy 910 supplied from the energy supply device 900. The energy 910 generated from the energy supply device 900 is irradiated to a side wall 110A and a bottom surface 110B of a second groove 120 of the first catalyst filter 100. Surfaces of the side wall 110A and bottom surface 110B of the second groove 120 to which the energy 910 is irradiated are activated, and thus a catalyst layer 410B is formed on the side wall 110A and bottom surface 110B of the second groove 120 and the second surface 110S. The catalyst layer 410B may be a layer or region that is activated by energy irradiation of the side wall 110A and bottom surface 110B of the second groove 120 and the second surface 110S.

In the first filtering system 1000 having the mechanism described above, a filtering process of a first material 920 and a second material 930, i.e., a process of removing the first material 920 and the second material 930 entering into the first catalyst filter 100, will be described. The first material 920 may include a particulate material. For example, the first material 920 may include particles. The particles may be, for example, particles having a particle diameter of about 10 micrometers (μm) or less, that is, fine particles of particulate matter 10 (PM10) or lower. The fine particles may include, for example, fine dust (i.e., microdust). The second material 930 may include a gaseous material, and examples of the gaseous material may include the VOC as described above. The second material 930 may include an organic compound. The first material 920 may not penetrate a horizontal part 410, which is a wall between the first and second grooves 110 and 120 and may not penetrate first and second vertical parts 415 and 425, and thus may accumulate on a wall of the first groove 110. Side walls and a bottom of the first groove 110 and a first surface 120S of the first vertical part 415 may all be referred to as a first surface of the first catalyst filter 100 that filters out the first material 920.

In the first catalyst filter 100, at least the horizontal part 410 may be a porous material layer that includes pores 410A. Therefore, the gaseous second material 930 may flow into the second groove 120 at least through the horizontal part 410, i.e., the side wall of the first groove 110. During this process, the second material 930 may generate a catalyst reaction as it passes the catalyst layer 410B and thus may be decomposed. For example, when the second material 930 includes formaldehyde ("HCHO"), the formaldehyde and oxygen in the second groove 120 may generate a catalyst reaction as the second material 930 passes the catalyst layer 410B and thus may be decomposed into water and carbon dioxide ($CO_2$). In this regard, the formaldehyde may be removed.

The energy supply device 900 may include an optical energy source that supplies photo energy in the form of light in a wavelength band from ultraviolet light to visible light, an ion energy source that supplies plasma, or a thermal energy source that supplies thermal energy in the form of infrared light. When the plasma is supplied from the energy supply device 900, the second material 930 and ozone in the second groove 120 may generate a catalyst reaction and thus may be decomposed.

Figure 11:
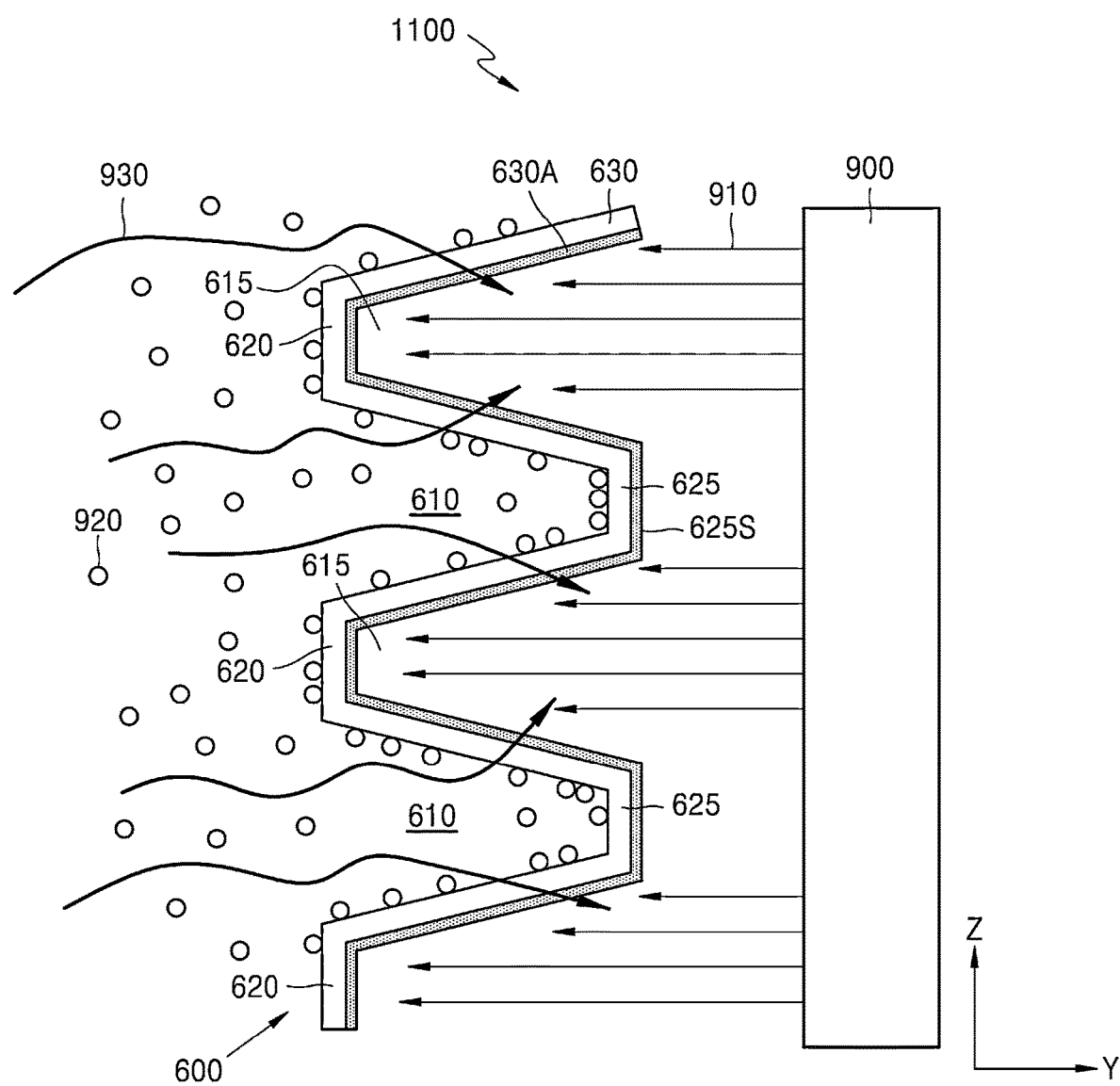
FIG. 11 is a cross-sectional view of the filtering system including the ceramic catalyst filter according to another embodiment.

FIG. 11 shows a second filtering system 1100 including the recyclable ceramic catalyst filter, according to another embodiment. Only parts different from the first filtering system 1000 of FIG. 10 will be described.

Referring to FIG. 11, the second filtering system 1100 includes a second catalyst filter 600 and an energy supply device 900. A second groove 615 of the second catalyst filter 600 faces the energy supply device 900. An inlet of the second groove 615 faces the energy supply device 900, and a diameter of the second groove 615 increases further along the (+) direction of the Y-axis. That is, a diameter of the second groove 615 increases further along toward the energy supply device 900. Accordingly, inner, side walls of the second groove 615 may all be exposed to an energy 910 supplied from the energy supply device 900. As a result, a surface of the second catalyst filter 600 facing the energy supply device 900 may be activated and thus form a catalyst layer 630A thereon. Therefore, the second material 930 passing the surface of the second catalyst filter 600 facing the energy supply device 900 may generate a catalyst reaction and thus be decomposed. In this regard, the surface of the second catalyst filter 600 facing the energy supply device 900, i.e., side walls and bottom of the second groove 615 and a second surface 625S of a second vertical part 625, may all be referred to as a second surface of the second catalyst filter 600 that removes the second material 930 or that changes the second material 930.

In the second filtering system 1100, a surface area of the surface of the second catalyst filter 600 facing the energy supply device 900 is relatively larger than a surface area of the first catalyst filter 100, and thus a surface area of the catalyst layer 630A formed in the second filtering system 1100 may be relatively larger than that of the first filtering system 1000. Accordingly, a filtering efficiency of the second filtering system 1100 may be relatively higher than that of the first filtering system 1000.

Figure 12:
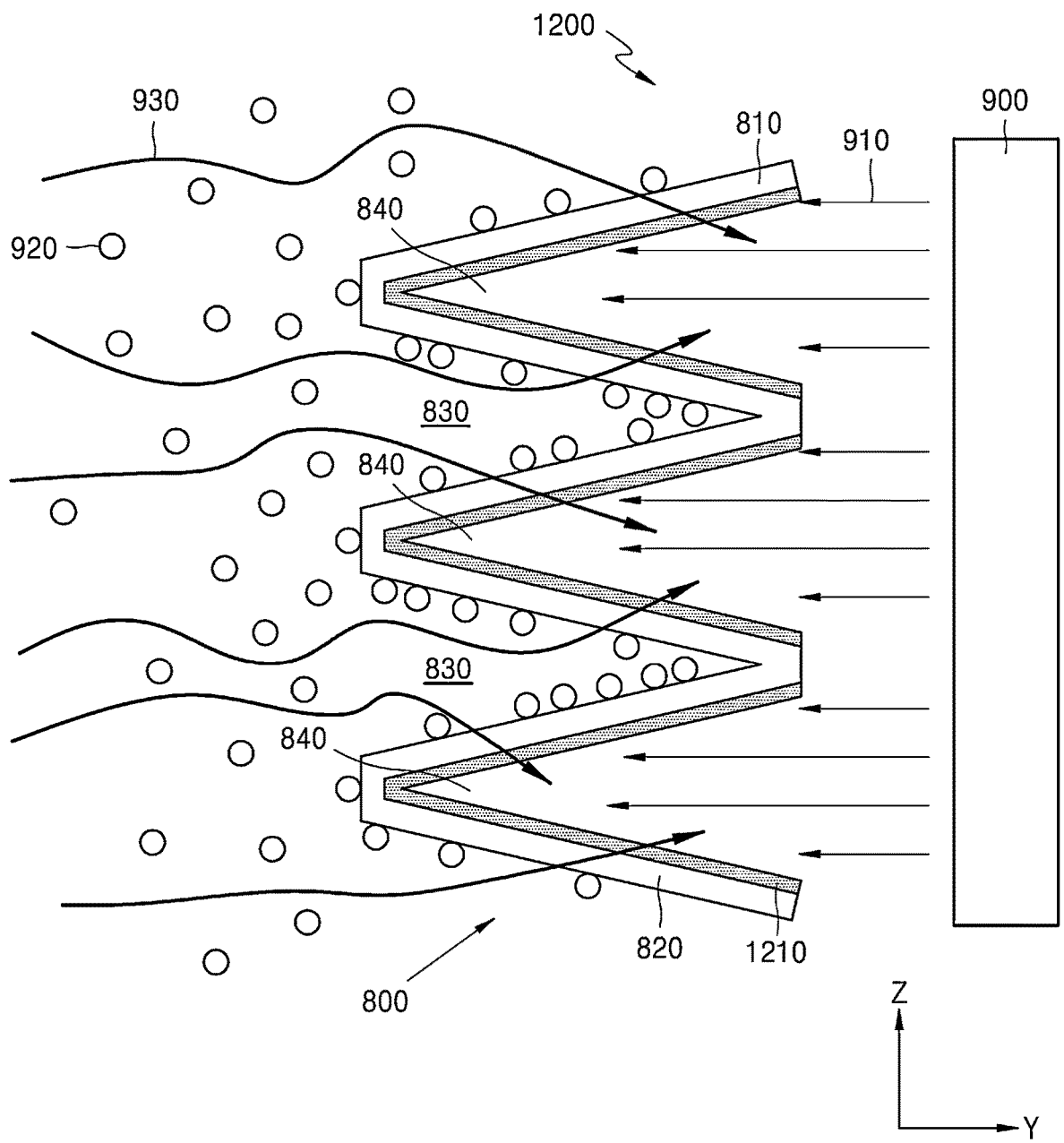
FIG. 12 is a cross-sectional view of the filtering system including the ceramic catalyst filter according to another embodiment.

FIG. 12 shows a third filtering system 1200 including the recyclable ceramic catalyst filter, according to another embodiment. Only parts different from the second filtering system 1100 of FIG. 11 will be described.

Referring to FIG. 12, the third filtering system 1200 includes a third catalyst filter 800 and an energy supply device 900. Configuration of the third filtering system 1200 may be the same as the second filtering system 1100 of FIG. 11, except that one end of the first inclined part 810 and one end of the second inclined part 820 contact each other directly. Inner side walls of a second groove 840 are all exposed to an energy 910 supplied from the energy supply device 910 in the same manner as in the second groove 615 of the second filtering system 1100. Accordingly, the inclined side walls of the second groove 840 are activated and thus may form a catalyst layer 1210 on the side walls.

Figure 13:
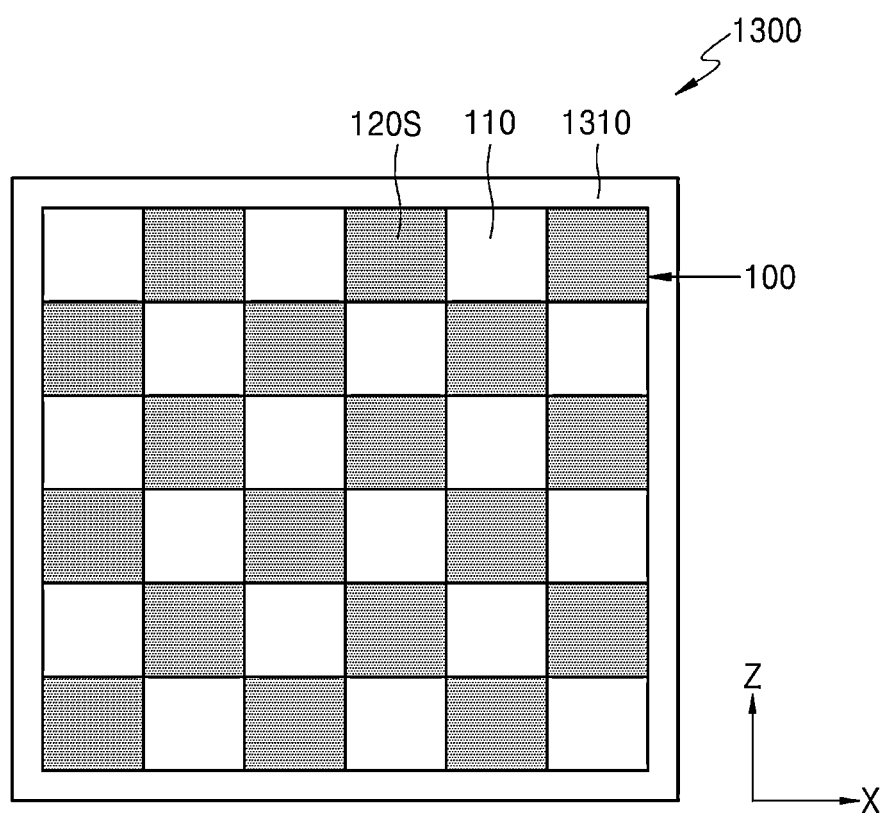
FIG. 13 is a front view showing a configuration when a circumference of the ceramic catalyst filter according to an embodiment is surrounded or covered with a heating member.

FIG. 13 shows a fourth filtering system 1300 according to another embodiment.

Referring to FIG. 13, the fourth filtering system 1300 includes a first catalyst filter 100 and a heating member 1310 surrounding the first catalyst filter 100. The heating member 1310 may cover the first catalyst filter 100 along an outer surface of the first catalyst filter 100. The heating member 1310 may include, for example, a heater that supplies heat to the inside of the first catalyst filter 100. The catalyst layer 410B as shown in FIG. 10 may be formed on an inner surface of the second groove 120 of the first catalyst filter 100 by the heat supplied from the heating member 1310.

Figure 14:
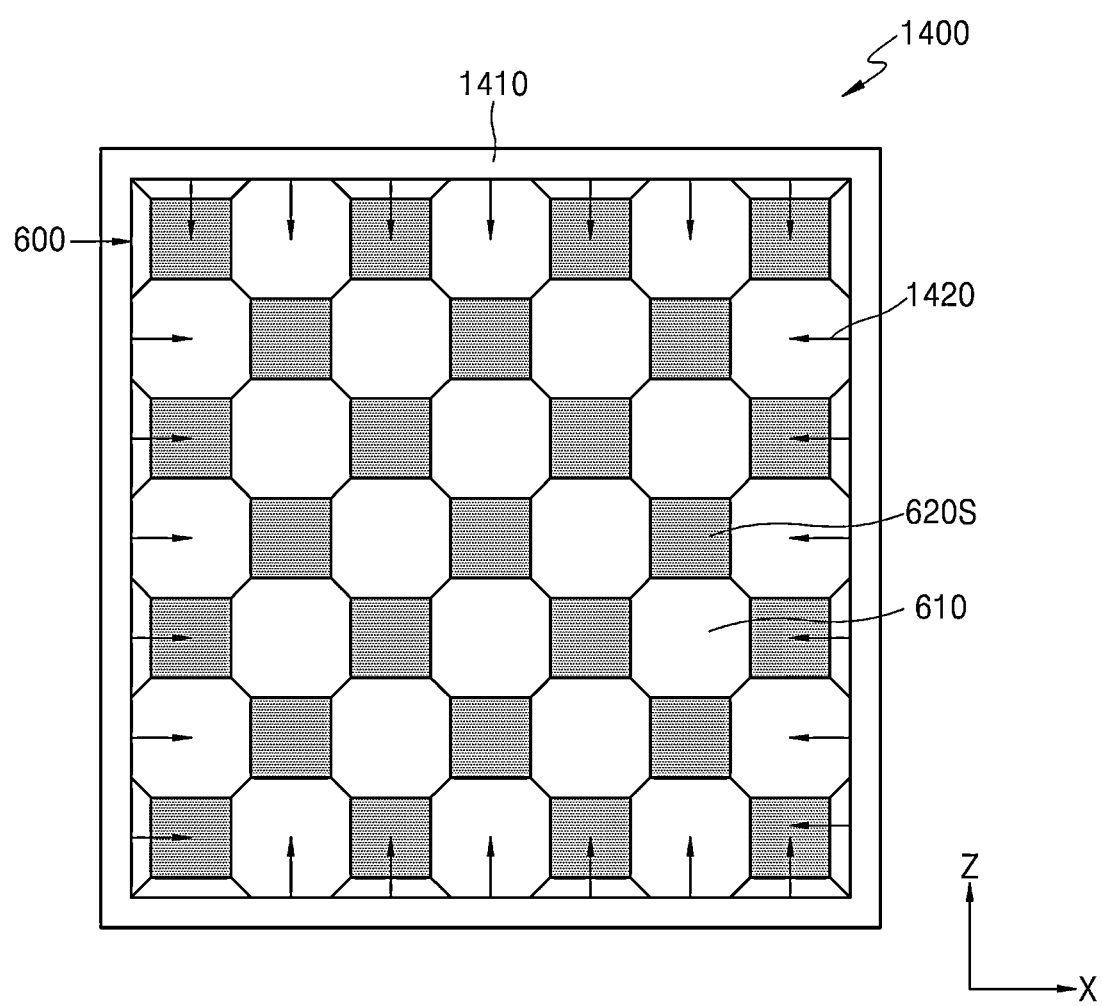
FIG. 14 is a front view showing a configuration when a circumference of the ceramic catalyst filter according to another embodiment is surrounded or covered with a heating member.

FIG. 14 shows a fifth filtering system 1400 according to another embodiment.

Referring to FIG. 14, the fifth filtering system 1400 includes a second catalyst filter 600 and a heating member 1410 surrounding the second catalyst filter 600. The heating member 1410 may be the same as or different from the heating member 1310 in FIG. 13. A thermal energy 1420 is supplied to the inside of the second catalyst filter 600 by the heating member 1410. The catalyst layer 630A as shown in FIG. 11 may be formed on side walls and bottom of the second groove 615 due to the thermal energy 1420.

Figure 15:
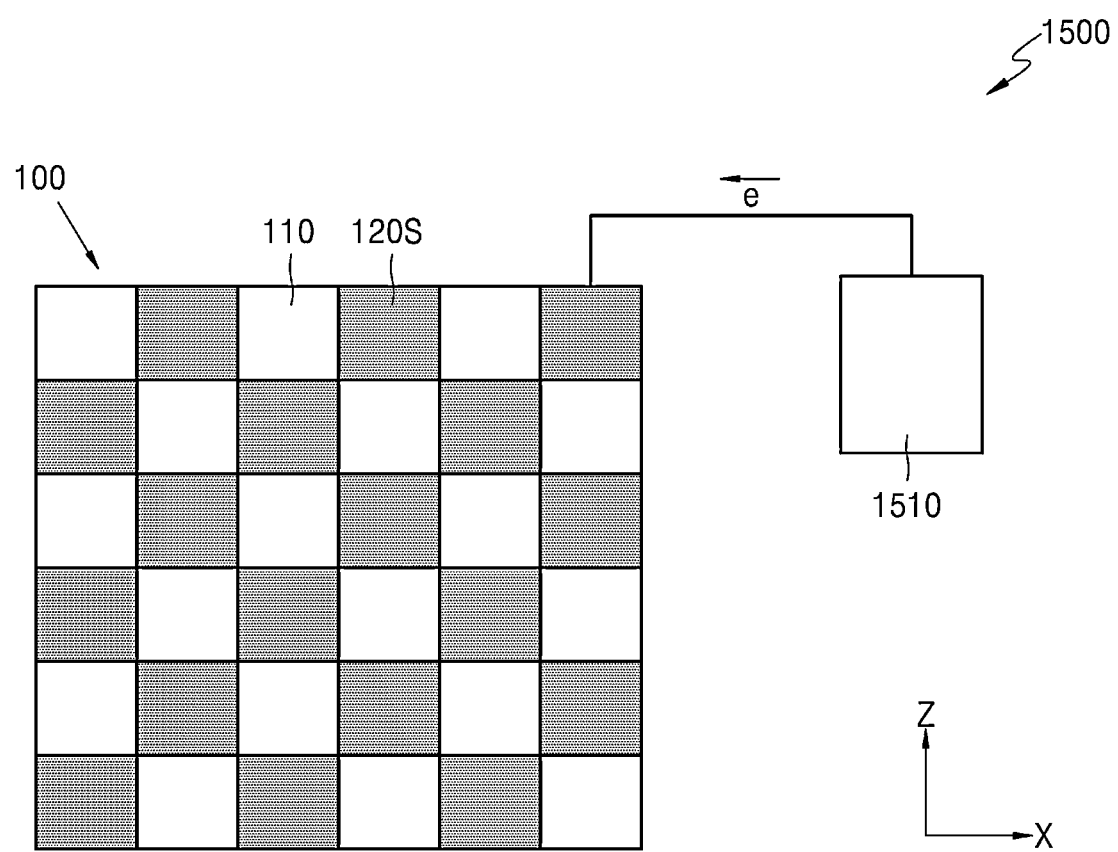
FIG. 15 is a block diagram illustrating a case when electric energy is supplied to the ceramic catalyst filter according to an embodiment, that is a case when a catalyst layer is formed on the ceramic catalyst filter by using an electric method.

FIG. 15 shows a sixth filtering system 1500 according to another embodiment.

Referring to FIG. 15, the sixth filtering system 1500 may include a first catalyst filter 100 and an anode 1510 that is electrically connected to the first catalyst filter 100. The first catalyst filter 100 may serve as a cathode. Here, the first catalyst filter 100 may be formed of or include a metal oxide that allows an electrically conductive ORR reaction. During the filtering process, electrons are supplied to the first catalyst filter 100 from the anode 1510, and this activates side walls of the second groove 120, which results a catalyst reaction. In some embodiments, a separate cathode layer that covers the side walls in the second groove 120 may be prepared.

Figure 16:
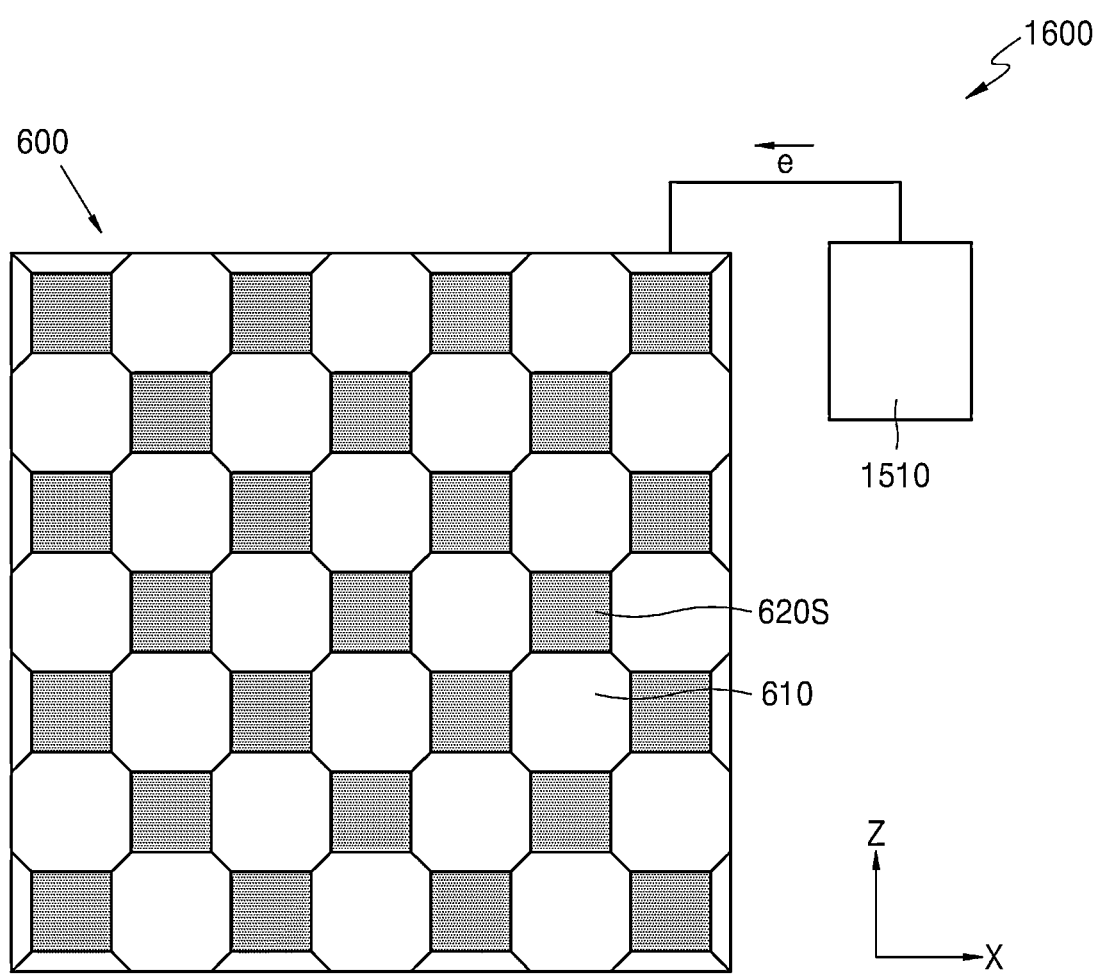
FIG. 16 is a block diagram of a case when electric energy is supplied to the ceramic catalyst filter according to another embodiment, that is a case when a catalyst layer is formed on the ceramic catalyst filter by using an electric method.

FIG. 16 shows a seventh filtering system 1600 according to another embodiment.

Referring to FIG. 16, configurations of the seventh filtering system 1600 are the same as the sixth filtering system 1500, except that the seventh filtering system 1600 uses a second catalyst filter 600 instead of the first catalyst filter 100.

Figure 17:
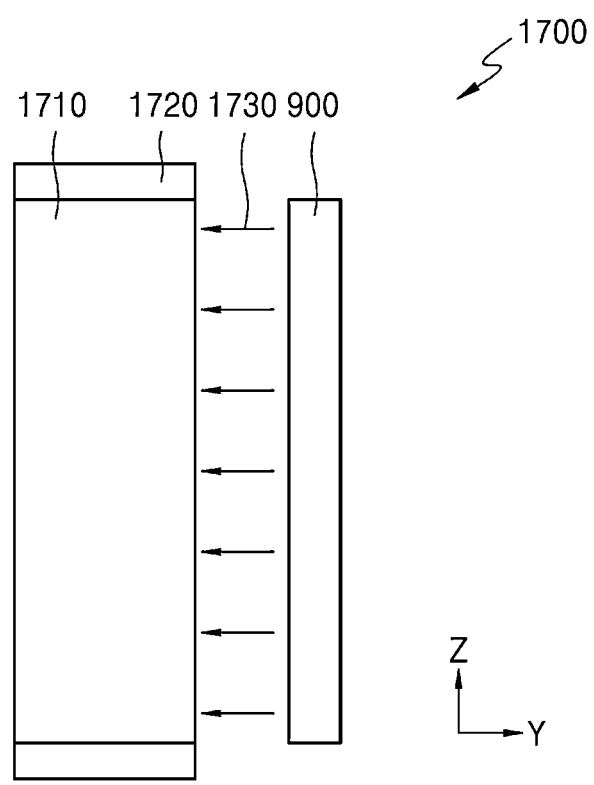
FIG. 17 is a cross-sectional view of a filtering system including a ceramic catalyst filter according to another embodiment.

FIG. 17 shows an eighth filtering system 1700 according to another embodiment. FIG. 17 illustrates an example of using multiple energy sources.

Referring to FIG. 17, the eighth filtering system 1700 includes a catalyst filter 1710, an energy supply device 900, and a heating member 1720. The catalyst filter 1710 may be one selected from the first to third catalyst filters 100, 600, and 800 described above. Here, a configuration of the single body frame (e.g., 645 in FIG. 8) of the selected catalyst filter may have the separate catalyst layer 470 shown in FIG. 6. Here, the catalyst layer 470 may be a photo-catalyst layer, and the single body frame 645 may be a thermal catalyst layer that generates a catalyst reaction by heat. The heating member 1720 is disposed along an outer surface of the catalyst filter 1710 and covers the catalyst filter 1710. The heating member 1720 may be the same as the heating member 1410 described in regard to FIG. 14.

During the filtering process, an optical energy 1730 is supplied to the catalyst filter 1710 from the energy supply device 900, and at the same time the heat from the heating member 1720 may be supplied to the catalyst filter 1710. In this regard, the catalyst layer 470 is activated by the optical energy 1730, and the single body frame 645 may be activated by the thermal energy supplied from the heating member 1720.

Hereinafter, a method of managing a filtering system including the recyclable ceramic catalyst filter according to an embodiment (hereinafter, also referred to as "a first management method") will be described.

Figure 18:
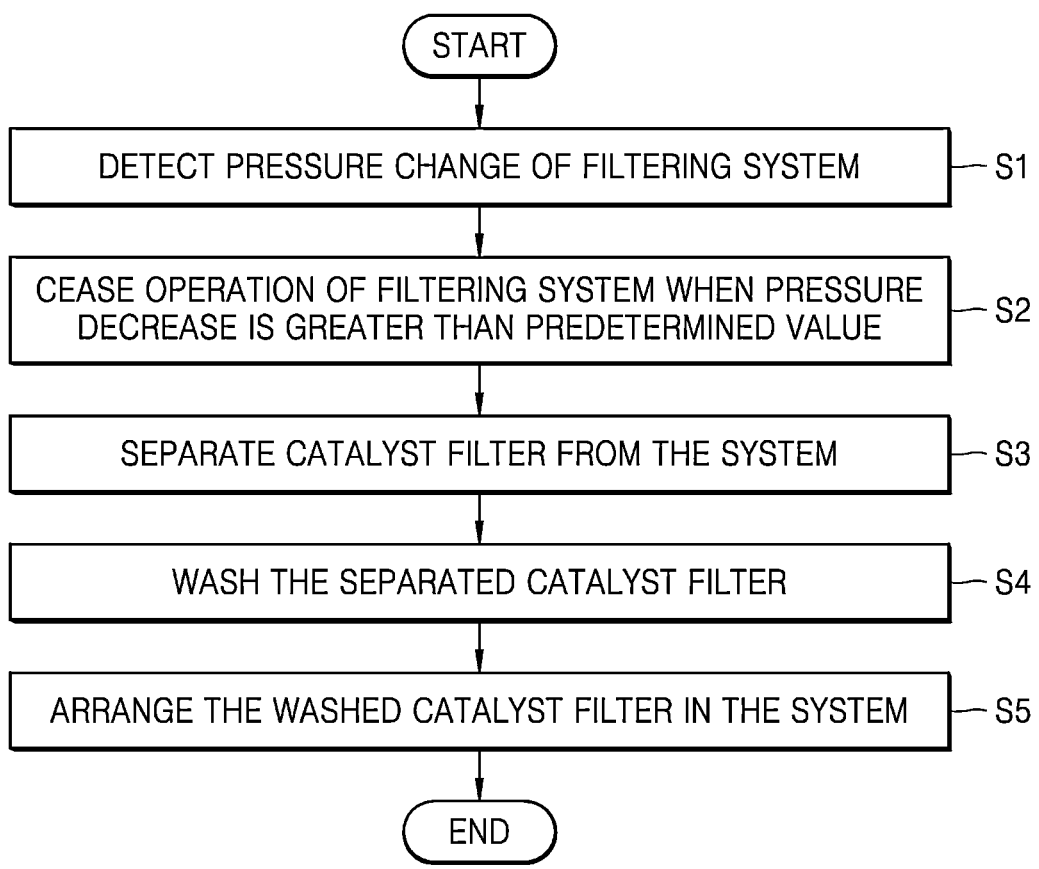
FIG. 18 is a flowchart showing steps of a method of managing a filtering system including the ceramic catalyst filter according to an embodiment.

Referring to FIG. 18, the first management method, first, detects a pressure change of the filtering system (S1). The filtering system may include one selected from the filtering systems shown in FIGS. 10 to 17. Next, once the pressure change is detected, when a pressure decrease is greater than the predetermined value, an operation of the filtering system ceases (S2). Here, ceasing the operation may include ceasing the entire operation by turning the power of the filtering system off and ceasing only the filtering operation while maintaining a basic pre-operation (e.g., a simple fan operation) of the filtering system. Also, the pressure decrease may denote a pressure decrease on a side (i.e., the gas discharge surface) where air of the ceramic catalyst filter is discharged. The detecting of the pressure change may include detecting a pressure difference between an air inlet and an air outlet of the catalyst filter. Based on the pressure difference, when the pressure difference is greater than or equal to the reference value, e.g., 250 pascals (Pa), the filtering system may be ceased.

After ceasing the filtering system, the ceramic catalyst filter is separated from the filtering system (S3). Thereafter, the separated ceramic catalyst filter is washed (S4). When an amount of the particulate first material 920 accumulates on the side walls and bottom of the groove (e.g., the first groove 610 in FIG. 11) on the air inlet side of the ceramic catalyst filter is greater than or equal to the reference amount, the pressure may decrease or the pressure difference may increase to higher than or equal to the reference value. Thus, in the washing (S4), the separated ceramic catalyst filter may be washed by using water or other predetermined solvent or solution to remove the accumulation or a particle cake on the catalyst filter.

After the washing of the ceramic catalyst filter, the washed ceramic catalyst filter is re-disposed on the filtering system (S5).

Hereinafter, a method of managing a filtering system including the recyclable ceramic catalyst filter according to another embodiment (hereinafter, also referred to as "a second management method") will be described.

Figure 19:
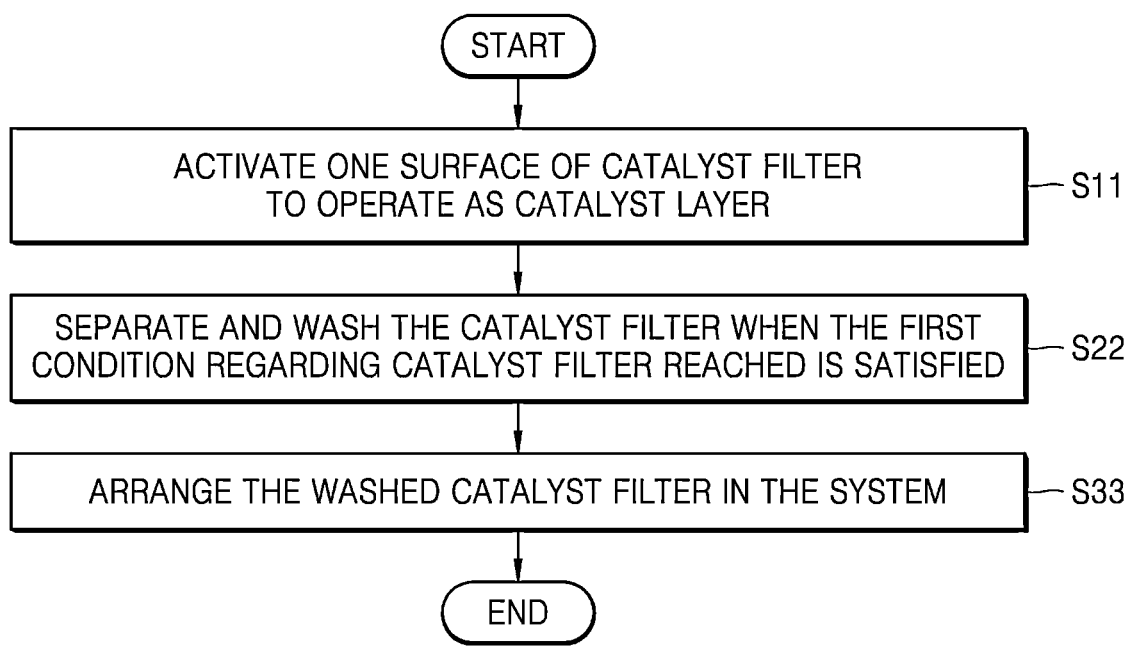
FIG. 19 is a flowchart showing steps of a method of managing a filtering system including the ceramic catalyst filter according to another embodiment.

Referring to FIG. 19, the second management method, first, activates one surface of a ceramic catalyst filter in the filtering system into a catalyst layer (S11). In the activating of the one surface of the ceramic catalyst filter (S11), a process of forming a catalyst layer on one surface of the ceramic catalyst filter may be performed by supplying an energy to the catalyst filter (e.g., 600 in FIG. 11) from the energy supply device 900 as described above.

Then, when the ceramic catalyst filter reaches a first condition, the ceramic catalyst filter separated and washed (S22). The first condition may be a condition described in relation to the pressure in the description of FIG. 18. After the washing of the ceramic catalyst filter, the washed ceramic catalyst filter is disposed to the original place (S33).

The disclosed ceramic catalyst filter forms a single body frame or a monolithic structure formed of or includes a catalyst material. Therefore, the disclosed ceramic catalyst filter does not need a separate support. Also, a single body filter frame in the disclosed ceramic catalyst filter has a wall-flow structure that filters particles among materials enter the catalyst filter and allows a gaseous component (e.g., VOC) to penetrate. In the process of the gaseous component passing the catalyst filter, energy is supplied to the catalyst filter, and a catalyst layer is formed on the catalyst filter by the energy. While the gaseous component passes the catalyst layer, the gaseous component is decomposed due to a catalyst reaction. As a result, according to one or more embodiments, when the catalyst filter is used, particle components along with a gaseous component such as VOC in the air may be simultaneously removed.

Also, when the disclosed ceramic catalyst filter is used, the removed particulate materials are accumulated on the side of inlets of the catalyst filter, and the particulate materials may impede a flow of the gaseous component. Therefore, the accumulated particulate materials need to be removed. In the disclosed catalyst filter, the filter frame itself is formed of or include a catalyst material, and thus the particulate materials accumulated on the catalyst filter may be simply removed by washing with a cleaning agent such as water. The catalyst filter from which the particulate materials are removed may be used again.

As described above, the disclosed ceramic catalyst filter may be used repeatedly, and thus it can reduce the consumption cost, reduce the resource consumption, and may be easily washed with a solvent or a solution such as water, thereby facilitating management.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A catalyst filter, the catalyst filter comprising:
a plurality of first grooves in which air is entered; and
a plurality of second grooves from which the air passed the first grooves is discharged and to which energy is provided from a front of the second grooves;
wherein the first grooves and the second grooves extend opposite directions from each other, and
first surfaces form an entire inside surface of the first grooves and second surfaces form an entire inside surface of the second grooves;
bottom surfaces of the first surfaces are disposed between inlets of the second grooves, and
the bottom surfaces of the first surfaces have a configuration that blocks a second material including a volatile organic compound, while side surfaces of the first surfaces have a configuration that passes the second material, wherein a catalyst material layer is between the first surfaces and the second surfaces, the catalyst material layer is a single layer, and the catalyst material layer comprises the first surfaces and the second surfaces, and wherein the second surfaces are activated by the energy.

2. The catalyst filter of claim 1, wherein the catalyst material layer comprises a porous material layer.

3. The catalyst filter of claim 1, wherein the first and second surfaces each comprise surfaces that are vertically or horizontally parallel to each other.

4. The catalyst filter of claim 1, wherein the air entered in the plurality of first grooves comprises a first material and the second material that are harmful and different from each other, and
wherein the first material comprises micro-dust.

5. The catalyst filter of claim 1, wherein the catalyst material is a photo-catalyst material, and the second surfaces are activated by an optical energy.

6. The catalyst filter of claim 1, wherein the catalyst material is an electric catalyst material, and the second surfaces are further activated by an electric energy.

7. The catalyst filter of claim 1, wherein the catalyst material is an ion catalyst material, and the second surfaces are further activated by an ion energy.

8. The catalyst filter of claim 1, wherein the catalyst material comprises a metal oxide.

9. The catalyst filter of claim 1, wherein bottom surfaces of the second surfaces are disposed between inlets of the first grooves.

10. The catalyst filter of claim 9, wherein air permeability of the bottom surfaces of the first surfaces and air permeability of the bottom surfaces of the second surfaces are different from each other.

11. The catalyst filter of claim 9, wherein a diameter of at least one of the first and second grooves decreases toward the bottom surfaces thereof from the inlets of the at least one first and second grooves.

12. The catalyst filter of claim 1, wherein a material layer between the first grooves and the second grooves has air permeability and allows the second material to permeate through the material layer.

13. The catalyst filter of claim 1, wherein the first and second grooves have each a wedge shape.

14. A filtering system comprising:
   the catalyst filter of claim 1; and
   an energy supply device which supplies energy for catalyst activation in the catalyst filter.

15. The filtering system of claim 14, wherein the energy supply device comprises at least one of an optical energy source, an electric energy source, an ion energy source, and a thermal energy source.

16. A catalyst filter, comprising:
   a plurality of first grooves in which air is entered; and
   a plurality of second grooves from which the air passed the first grooves is discharged;
   wherein the first grooves and the second grooves extend opposite directions from each other,
   wherein first surfaces form an entire inside surface of the first grooves and second surfaces form an entire inside surface of the second grooves, where one of the first grooves is surrounded by four first surfaces and one of the first surfaces is surrounded by four first grooves;
   a material layer is disposed to include surfaces defining the second grooves, and includes a thermal catalyst material, and
   the second surfaces are activated by a thermal energy provided from a front of the second grooves; and
   wherein a catalyst material layer is between the first surfaces and the second surfaces, the catalyst material layer is a single layer, and the catalyst material layer comprises the first surfaces and the second surfaces.

17. The catalyst filter of claim 1, wherein the first surfaces of the plurality of first grooves are connected each other and the second surfaces of the plurality of second grooves are connected each other.

18. The catalyst filter of claim 1, wherein the plurality of first grooves are arranged in a first direction and a second direction perpendicular to the first direction, and
   wherein the plurality of first grooves are separated in the first and second directions.

19. The catalyst filter of claim 1, wherein areas of the inlets of the plurality of second grooves are the same as or different from areas of inlets of the plurality of first grooves and areas of bottoms of the plurality of the first grooves are the same as or different from areas of bottoms of the plurality of second grooves.

* * * * *